(12) United States Patent
Loewenthal et al.

(10) Patent No.: US 6,395,918 B1
(45) Date of Patent: May 28, 2002

(54) CONVERSION OF A HYDROXY GROUP IN CERTAIN ALCOHOLS INTO A FLUOROSULFONATE ESTER OR A TRIFLUOROMETHYLSULFONATE ESTER

(76) Inventors: Hans Jacob Edgar Loewenthal; Ron Benjamin Loewenthal, both of Horev Street 78, Achuza 34343 Haifa (IL)

( * ) Notice: Subject to any disclaimer, the term of this patent is extended or adjusted under 35 U.S.C. 154(b) by 0 days.

(21) Appl. No.: 09/697,740

(22) Filed: Oct. 27, 2000

Related U.S. Application Data

(63) Continuation-in-part of application No. PCT/IL99/00165, filed on Mar. 24, 1999.

(30) Foreign Application Priority Data

Apr. 27, 1998 (IL) .................................................. 124235

(51) Int. Cl.[7] .......................................... C07C 307/02
(52) U.S. Cl. ..................................................... 558/54
(58) Field of Search ..................... 562/109, 37; 564/98; 568/54

(56) References Cited

FOREIGN PATENT DOCUMENTS

| ES | WO 99/23064 A1 * | 5/1999 |
|---|---|---|
| GB | 1 469 727 | 4/1977 |
| GB | 1 494 436 | 12/1977 |

OTHER PUBLICATIONS

Piccolo et al, Stereospecific Friedel–Crafts Alkylation of Aromatic Compounds: Synthesis of Optically Active 2– and 3– Arylalkanoic Esters, Journal of Organic Chemistry 1991, 56, pp. 183–187.*

Berner et al., 203. 1,2–Shift of a Carboxyl Group in a Wagner–Meerwein Rearrangement, *Helvetica Chimica Acts*, vol. 65, Fasc. 7, No. 203, pp.2061–2070.

Zefirov et al., "Novel Method of Deoxidation of Alcohols and its use in synthesis of Convalent Perchlorates", *Tetrahedron Letters*, vol. 26, No. 50, pp. 6243–6245, (1995).

Frederick et al., "Betylates. 2. The formation and high reactivity of alkyl [0]betylates", *Canadian Journal of Chemistry*, vol. 59, No. 2, pp. 362–373, (1981).

Spilane et al., "Versatile Synthesis of Sulphamate Esters by Phase–tranfer Method", *J.C.S. Perkin I*, pp. 677, (1982).

Mason et al., The O–Alkylation of 5–Hydroxy Chromes, A Comparison of two Non–Classical Technique, PTC in the Absence of Solvent and Sonochemical Activation in Polar Aprotic Solvents, *Synthetic Communications*, vol. 20, No. 22, pp. 3411–3420, (1990).

Takai et al., "Acyclic Stereoselection, 32. Synthesis and Characterization of the Diastereomeric (4S)–Pantane–1,2,3, 4,–tetrols", *The Journal of Organic Chemistry*, vol. 50, No. 18, pp.3247–3251, (1985).

Mattell, "Stereochemical studies on plant growth regulations. VII", *Arkiv Kemi*, vol. 6, pp. 365–373, (1953).

Clinton et al., "The Preparation of Methyl Esters", *J. Amer. Chem. Soc.*, vol. 70, pp. 3135–3137, (1948).

(List continued on next page.)

*Primary Examiner*—Gary Geist
*Assistant Examiner*—Paul A. Zucker
(74) *Attorney, Agent, or Firm*—Browdy and Neimark, P.L.L.C.

(57) ABSTRACT

The present invention provides a method of converting a hydroxy group in alcohols containing an electron withdrawing group into perfluoroalkane sulfonate and fluorosulfonate esters, which are good leaving groups, with inversion of configuration where the hydroxyl-bearing carbon is chiral. The method consists of converting an alcohol to an O—N, N-dialkylsulfamate ester and reacting it with a perfluoroalkansulfonic or fluorosulfonic acid. The method has applications in the synthesis of pharmaceutical and agrochemical compounds.

25 Claims, 2 Drawing Sheets

OTHER PUBLICATIONS

Feenstra et al., "An efficient Synthesis of N–Hydroxy-α–Amino Acid Derivatives of High Optical Purity", *Tetrahedron Letters*, vol. 28, pp. 1215–1219, (1987).

Buncel, "Chlorosulfates", *J. Chem. Soc.*, vol. 10, No. 97, (1969).

Stang et al., "Perfluoroalkanesulfonic Esters: Methods of Preparation and Applications in Organic Chemistry", *Synthesis*, pp. 85–87, (1982).

* cited by examiner

Racemic Mixture

CONVERSION OF A HYDROXY GROUP IN CERTAIN ALCOHOLS INTO A FLUOROSULFONATE ESTER OR A TRIFLUOROMETHYLSULFONATE ESTER

This application is a continuation-in-part of copending parent application Ser. No. PCT/IL99/00165, filed Mar. 24, 1999.

FIELD OF THE INVENTION

The present invention is in the field of organic chemistry. More particularly, the present invention provides a new method of converting a hydroxy group in certain alcohols into a good leaving group and that with inversion of configuration where the hydroxyl-bearing carbon is chiral. Such a method is particularly useful for preparing chiral compounds for pharmaceutical and agrochemical use.

BACKGROUND OF THE INVENTION

Government regulations in various countries, especially in the U.S., have raised the necessity of finding an economical way for the production of the more active enantiomer of a drug whose molecule is chiral, other than by resolution of the racemic final (or intermediate) product, by the use of expensive chiral catalysts or auxiliaries—usually of the non-recoverable or partially recoverable kind, or by the discovery of an enzymatic process. To satisfy this necessity three requirements must be met [see A. N. Collins, G. M. Sheldrake, and J. Crosby (Eds.), Chirality in Industry (1992), and Chirality in Industry II (1997), John Wiley & Sons, Chichester]. The first one is to select an inexpensive, preferably naturally occurring starting material, from a renewable source, which can be elaborated to the desired product enantiomer. The second requirement is to ensure that during this elaboration chirality of the intermediates is maintained, and that relative stereochemistry, during possible introduction of further chiral centers, is predictable. The third requirement is that yields as high as possible are achieved during this elaboration, with minimal expense of auxiliary reagents, so as to make the whole process economically feasible.

Preferred such naturally occurring chiral compounds are esters derived from lactic acid (in particular the ethyl and methyl esters), because such esters are inexpensive and available in large amounts. This invention refers mainly to these esters, but is equally applicable to other alkyl lactates, as well as to esters of other naturally occurring chiral α-hydroxy acids such as malic acid or mandelic acid and in general to compounds having a hydroxyl group attached to a chiral carbon atom.

α-Hydroxycarboxylic acids are important starting materials for pharmaceutically and agrochemically important compounds, particularly when they contain a chiral carbon atom in the molecule. In the more abundant form of all these α-hydroxycarboxylic acids the carbon atom attached to the hydroxyl group has the S-absolute configuration. However, they also occur or are commercially available with this carbon atom having the R-configuration (see G. M. Coppola and H. F. Schuster, α-Hydroxy Acids in Enantioselective Synthesis, VCH-Wiley, Weinheim, 1997; A. N. Collins, G. M. Sheldrake, and J. Crosby, Eds., Chirality in Industry II, Wiley, 1997, Chapter 10).

It is well known that $SN_2$ substitution reactions at an asymmetric carbon proceed with inversion of configuration. When such substitution takes place at the chiral carbon next to the hydroxyl group in a chiral alcohol, a clean inversion of configuration occurs (as schematically shown in FIG. 1), with retention of chirality. In $SN_2$ reactions the hydroxyl group has to be converted into the best possible leaving group L. However, both L and the incoming nucleophile group Nu are negatively charged (or electron-rich) and if there is little difference between the two in this respect, they can exchange roles and the reaction can go in the opposite direction. In that case chirality may be lost because at the intermediate stage the carbon is connected neither to Nu nor to L, thus being trihedral and planar. Each group can enter and leave from either direction leading to racemisation (as schematically shown in FIG. 2) and elimination. The difference between the nucleophility of the two groups is a function of the relative acid strengths of the two corresponding acids Nu-H and L-H.

In order to avoid racemisation and elimination, the hydroxyl group has to be converted into a good leaving group, such as, for example, an ester of a sulfonic acid. The most common sulfonic acids are methanesulfonic acid, benzenesulfonic acid and p-toluenesulfonic acid. However, trifluoromethylsulfonic acid and fluorosulfonic acid are among the strongest known sulfonic acids and are of the order of $10^4$ stronger than toluene- and benzenesulfonic acids (see P. J. Stang, M. Hanack and L. R. Subramanian, Synthesis 1982, 85).

Hence, in order to fulfill the above requirements, i.e. maximum retention of chirality in a predictable manner and highest possible yields resulting from absence of side reactions such as elimination, organic chemists have for many years tended to use in particular trifluoromethylsulfonate (hereinafter "triflate") esters of hydroxyl groups as leaving groups in such substitution reactions. The main problem is the high cost of trifluoromethylsulfonic acid, in particular when considering the fact that to make esters of trifluoromethylsulfonic acid, one has to use its anhydride which is made from two molecules of the acid, only one of which ends up in the ester. On the basis of current prices, the process of triflation of an hydroxyl group is more than 56 times the cost of toluenesulfonation ("tosylation") and 35 times the cost of benzenesulfonation (ignoring the cost of solvents, amine bases which have to be of the more expensive hindered type in case of triflation, and not counting the possible recovery of the other molecule of triflic acid which is a rather involved process). If only one equivalent of trifluoromethylsulfonic acid itself could be used, the cost difference would drop to ca. 28 times that of tosylation. However, no method is known in the prior art for carrying out such a reaction.

The situation with fluorosulfonate esters is more complex and intriguing. The acid itself is used in other industrial applications, and is presently available in tank loads at a very low price. If it were possible to use it, rather than its anhydride, the cost of fluorosulfonation could be practically identical to that of tosylation or mesylation, and perhaps even cheaper. However, no method is known in the prior art for carrying out such a reaction. The anhydride itself is very difficult to prepare, is very volatile and is poisonous (of the same order as phosgene). It has recently been offered for sale at a price which would make fluorosulfonation over 200 times more expensive than tosylation, apart from the additional hazards involved.

Can. J. Chem. 59(2), 1981, 362–372 describes the reaction of N,N-dimethylsulfamates with methyl fluoro (trifluoromethane) sulfates.

It is an object of this invention to provide an efficient and economical method for the preparation of fluorosulfonic and perfluoroalkanesulfonic esters of hydroxy compounds.

It is another object of this invention to provide such a method by which such esters of chiral starting materials can be prepared in good yield, with inversion of configuration and maximal retention of chirality in the resulting product.

It is a further object of this invention to provide such a method that is particularly useful in the case of carboxylic esters of lactic acid.

Other objects and advantages of the invention will become apparent from the description of the invention.

SUMMARY OF THE INVENTION

The present invention provides a method of substituting a hydroxyl group attached to a chiral carbon atom bearing an electron withdrawing group such as carboxylic ester, carbonyl or cyano in a hydroxy compound with a leaving group selected from fluorosulfonate and perfluoroalkylsulfonate, which comprises the steps of:

(a) converting said hydroxyl group to an O—N,N-dialkylsulfamate ester thereof, and (b) reacting said O—N,N-dialkylsulfamate ester, optionally in a suitable inert solvent, with 1±0.2 equivalent of either perfluoroalkylsulfonic acid or fluorosulfonic acid.

The substitution occurs with inversion of configuration and substantial retention of chirality.

As used herein the term "alkyl" refers to a linear, branched or cyclic alkyl group having up to and including 12 carbon atoms.

The dialkylsulfamate ester is prepared from the starting hydroxy compound by one of three possible methods:

Method A: Formation of the O-chlorosulfonate ester by reaction with sulfuryl chloride, followed by replacement of the chlorine by a dialkylamino group under suitable conditions.

Method B: Formation of the O-monoalkylaminosulfamate ester by reaction with a monoalkylaminosulfamyl chloride and a base, followed by N-alkylation of the amino group.

Method C: Direct reaction of an O-metal derivative of the hydroxy compound with a dialkylsulfamyl chloride.

The reaction in step (b) above is preferably carried out in an inert solvent at between about −50° C. and about +30° C. The only byproduct is the dialkylsulfamic acid, most of which precipitates from the reaction mixture and can easily be removed e.g. by filtration or centrifugation.

DETAILED DESCRIPTION OF THE INVENTION

Figure 1:
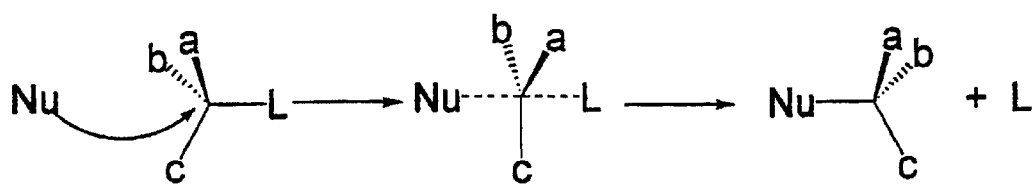
FIG. 1—Scheme of general $SN_2$ type reaction resulting in inversion of configuration.
Figure 2:
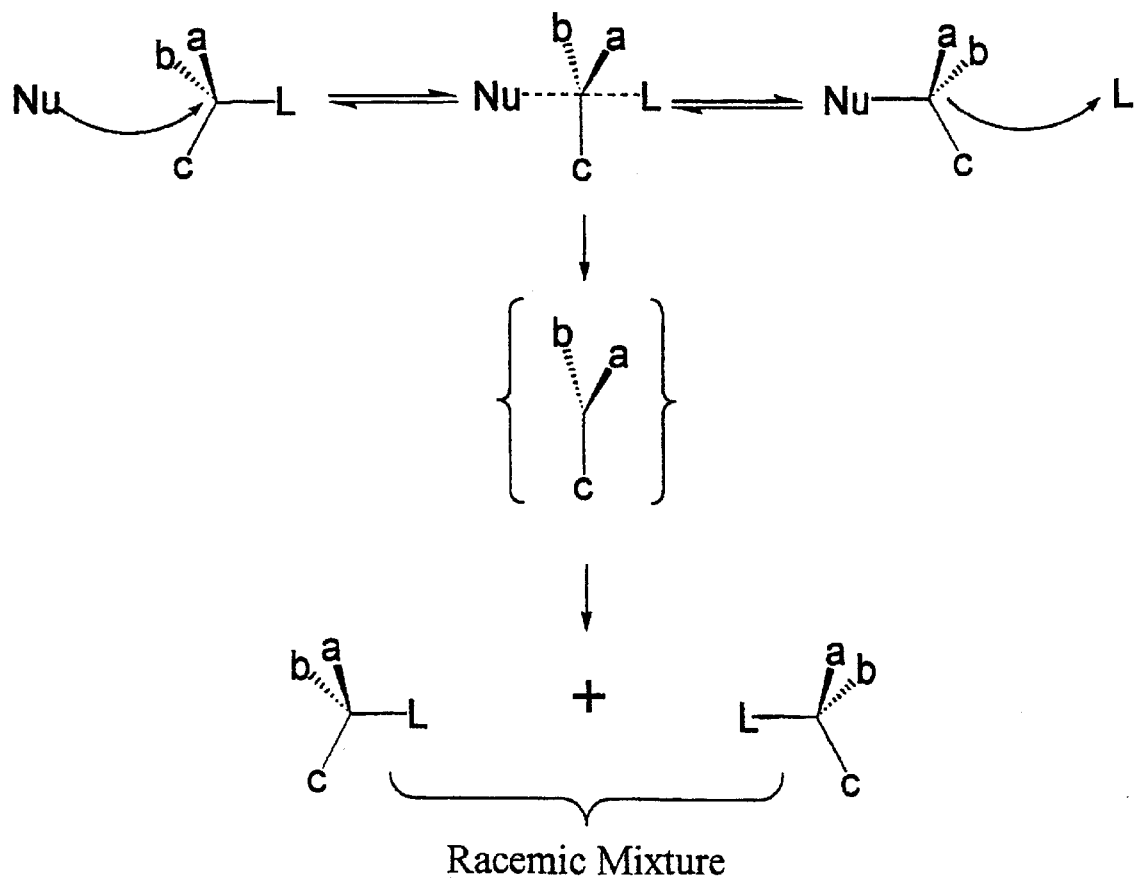
FIG. 2—Scheme of $SN_2$-type reaction resulting in racemisation.
Figure 3:
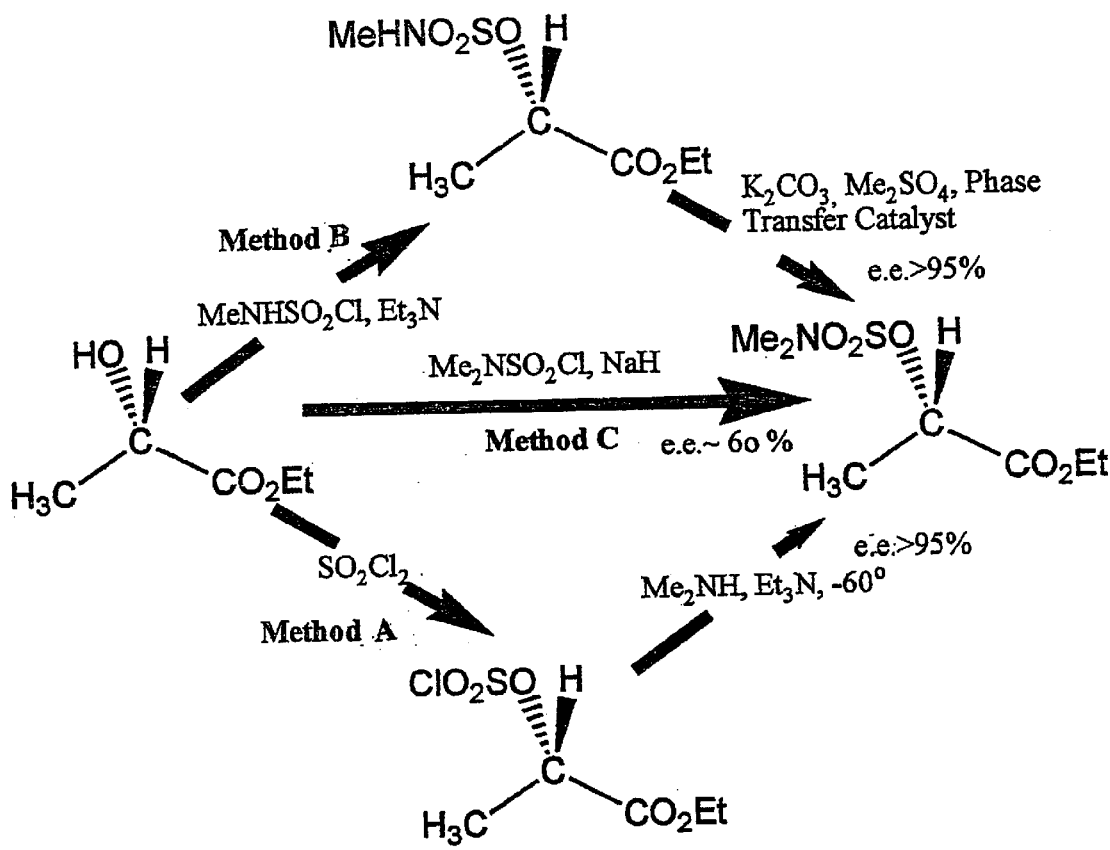
FIG. 3—Methods A, B, and C for the preparation of O—N,N-dialkylsulfamyloxy derivatives of esters of lactic acids, shown specifically for the N,N-dimethyl derivative and starting from (S)-ethyl lactate.
Figure 4:
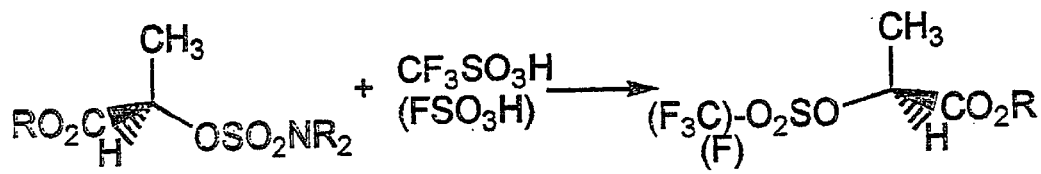
FIG. 4—Scheme of substitution of dialkylsulfamyloxy derivatives by either trifluoromethylsulfonic acid or fluorosulfonic acid, with inversion of configuration.

The first step of the method of the present invention is the preparation of an O—N,N-dialkylsulfamyl ester, particularly of an alkyl lactate. Preferably, this sulfamate is an O—N,N-dimethylsulfamyl ester. N,N-Dimethylsulfamyl esters can be prepared by three alternative methods (as schematically shown in FIG. 3 as Methods A, B and C), all three already known in principle from the literature with reference to other hydroxylic compounds.

Method A begins with reaction between an alkyl lactate and sulfuryl chloride at or below room temperature, with constant removal of the hydrogen chloride formed, best by a slow gas stream. This results in the formation of the O-chlorosulfonate in high yield. This intermediate need not be isolated and can be used for the next step after completely removing all excess reagent and hydrogen chloride in vacuo. Chlorosulfonate esters have been discussed in a review (E. Buncel, Chem. Revs. 1970, 70, 323) according to which their reactions with nucleophiles tend to be varied, unpredictable and generally of little synthetic value. Thus, with a dialkylamine such as dimethylamine the product might be simply that of replacement of chlorine alone by dimethylamino (the desired reaction), or an internal displacement ($SN_i$) by chlorine at carbon to give a chloro compound, or an $SN_2$ displacement at carbon by the dimethylamine to give an amine. It has now been found, and this finding is an important part of the invention, that the first pathway is strongly favored over the other two by the right choice of reaction solvent(s) and by conducting the reaction at as low a temperature as practicable. Thus, in practice, the crude chlorosulfonate ester, after being vacuum-treated, is dissolved in dichloromethane, the solution cooled below −60° and, with stirring, a solution of a slight excess of both dimethylamine and triethylamine or of 2.4 equivalents of dimethylamine alone in gaseous form, in a solvent such as toluene or chloroform is added. Upon addition of water, drying and distillation, the O-dimethylsulfamate ester of the lactate ester is obtained in good overall yield. Apart from its simplicity further advantages of this pathway are the low cost of the reagents used and the fact that the entire sequence can be conducted in the same vessel. A further, and most important aspect of this route is that practically no epimerisation takes place.

Method B comprises reaction of the lactate ester with a monoalkylsulfamyl chloride (preferably the monomethyl compound) in the presence of a tertiary amine to combine with the HCl liberated. This reaction occurs smoothly, since the true reactive intermediate is not the chloride itself but the sulfonyl-imine $CH_3-N=SO_2$ (formed through dehydrochlorination by the tertiary amine present) which is highly reactive and adds electrophilically to the hydroxyl group of the lactic ester; here too epimerisation at carbon is reduced to a minimum. The reaction product need not be purified but can be further methylated by a phase transfer reaction (see W. J. Spillane, A. P. Taheny, and M. M. Kearns, J. C. S. Perkin I, 1982, 677). In the case of the N-monomethyl sulfamate methyl ester, this can be reacted with the cheap reagent dimethyl sulfate, an alkaline carbonate and a phase transfer catalyst in an inert solvent or solvent system, again without epimerisation. The overall yield in this method is about the same as in Method A. With the N-monomethyl sulfamate ethyl ester, in the second part of this two-step process, partial transesterification of the carboxyl ester group may be a complicating factor, but this can be avoided completely by judicious choice of solvent and phase transfer catalyst (for a similar case see T. J. Mason et al, Syn. Comm. 1990, 20, 3411).

Method C appears to be the shortest method: direct reaction of the ester of lactic acid with a dialkylsulfamyl chloride, preferably dimethylsulfamyl chloride, in the presence of a base. However, since dimethylsulfamyl chloride is rather unreactive, this reaction has to be carried out with the metal alcoholate of the lactic ester, which is formed e.g. by the action of sodium hydride. This, however, leads to partial racemisation at the chiral carbon (see K. Takai and C. H. Heathcock, J. Org. Chem. 1985, 50, 3247). A modification of this sequence involving the slow addition of the sodium hydride to a mixture of the lactic ester and the dimethylsulfamyl chloride at a low temperature leads to a product which at best is of 60% optical purity. As against this, the chemical overall yield is higher than in the previous two methods.

Step (b) in the method of the invention consists in the conversion of O—N,N-dialkylsulfamate esters, particularly of alkyl lactates, into O-trifluoromethylsulfonyl or O-fluorosulfonyl esters. As stated above, this is done by the reaction of said dialkylsulfamate ester, preferably in a solvent, with 1±0.2 equivalent of either trifluoromethanesulfonic acid or of fluorosulfonic acid.

In principle, any solvent that does not react with the sulfonic acid employed can be used in step (b), for example saturated hydrocarbons and saturated halogenated hydrocarbons. Chlorinated hydrocarbons are especially preferred. Carbon tetrachloride and trichloroethylene are preferred solvents (with the latter being more environmentally friendly), because both sulfonic acids and also the by-product dimethylsulfamic acid are insoluble in these solvents whereas both starting material and product are freely soluble. The reaction, conducted with vigorous stirring or agitation between 0° C. and room temperature proceeds by interaction between two phases. At the beginning these are two liquid phases but as the reaction proceeds, a suspension of crystalline dimethylsulfamic acid in the product or solution of the product is formed. At the end of the reaction the sulfamic acid byproduct, formed in practically theoretical yield, can be filtered off and recycled.

Preferred hydroxy compounds used in the present invention are esters of naturally occurring α-hydroxy carboxylic acids such as lactic acid, malic acid and mandelic acid. Particular reference in describing the invention will be made to esters of lactic acid but this should not be construed as a limitation.

Experimental results suggest that: (a) the reaction with the sulfonic acid is of the regular $SN_2$ type, (b) the leaving group is the internally stabilized zwitterion $R_2HN^+$—$SO_3^-$, and (c) that this is the first recorded instance that anions derived from strong acids such as trifluoromethanesulfonic or fluorosulfonic acids act as nucleophiles; and that thus the aforementioned zwitterion is the best leaving group so far discovered. As for (a), this is evident by the fact that inversion occurs during the reaction; and regarding (b), by the fact that the desired reaction does not take place when one or both of the R groups on the nitrogen atom is aromatic, being well known that such a nitrogen atom is less basic than when it is alkyl-substituted and is less disposed to accept a proton from the —$SO_3H$ of the sulfonic acid; hence the derived zwitterion is less internally stabilized.

Another sequence showing that in principle the method of the present invention is more generally applicable, is that starting with dimethyl S-malate. Displacement of the dimethylsulfamate group in the intermediate thereof with fluorosulfonic acid has been found to proceed normally and with inversion, as in the case of lactic esters.

The method of the invention is useful for preparing chiral compounds for both pharmaceutical and agrochemical use. For example, in the pharmaceutical field, an important group of anti-hypertensive drugs are the A.C.E. (Angiotensin Converting Enzyme) inhibitors. Among these are some of the most widely prescribed drugs in the world. There are approximately 18 of these on the market, and the majority of these show one common feature in their molecular structure: a distinction can be made between the "left-hand side" and the "right-hand side" of the molecule. The latter is different in each of these drugs and will not be discussed further here. On the other hand, it is the "left-hand side" which is the same in all of them. That part of the molecules is 4-phenylbutanoic acid (in the form of its ethyl ester), which is linked at the 2-position via an amino nitrogen atom to the "right-hand side". The substitution at position 2 in these compounds creates an asymmetric center at that carbon and the absolute configuration there is of the (S)-type following the universally accepted CIP convention. In practice, most synthetic paths to these A.C.E. drugs involve connection of the "left-hand" and "right-hand" parts, by nucleophilic substitution of a leaving group at C2 in the former by an amino group in the latter. This type of reaction invariably occurs with inversion of configuration, and therefore C2 in the "left-hand side" with its leaving group must have the (R)-configuration prior to that substitution reaction. Such leaving groups are nearly always sulfonates of hydroxy groups, formed with retention of configuration, and in practice, even on an industrial scale, the sulfonate group chosen is trifluoromethanesulfonate, using the anhydride, in view of the high yields and stereochemical integrity experienced with this leaving group, and that in the face of the very high cost involved.

According to the present invention, the hydroxy group in the 2-hydroxy-phenylbutanoic ethyl ester required can now be converted into a fluorosulfonate instead of the expensive triflate, via one of the routes described above. Furthermore, in view of the inversion of configuration which we have discovered, it is the (S) starting ester which is required as starting material rather than the (R) usually used for that α-hydroxycarboxylic ester. Among the three methods mentioned earlier, Method B (N-methylsulfamyl chloride, triethylamine, dichloromethane solvent) was found to be the most suitable.

The N-methylsulfamate formed was further methylated as described above and shown schematically in FIG. 3, to give the N,N-dimethylsulfamate. Both these intermediates need practically no purification, and the reactions can easily be monitored by TLC. Subsequent reaction with fluorosulfonic acid, in 1,2-dichloroethane, provides the dextrorotatory O-fluorosulfonate derivative which can be short-path-fractionated. Reaction of this with (S)-alanine benzyl ester, for example, followed by catalytic debenzylation gives the crystalline (S,S)-N-(1-ethoxycarbonyl-3-phenylpropyl) alanine, one step away from the well-known A.C.E. inhibitor Elanapril. The properties of this intermediate (melting point, n.m.r. spectrum, specific rotation) were in excellent agreement with those published (H. Urbach, R. Henning, Tetrahedron Lett. 1984, 25, 1143).

In the following Examples, optical rotations were measured in substance unless a solvent is mentioned, and at a wavelength of 589 nm, and are in most cases corrected for density, i.e. as specific rotations when in square brackets [α] I..R. spectra are in $cm^{-1}$ for liquid films unless otherwise indicated; and n.m.r. spectra were done in $CDCl_3$ and peaks are given in p.p.m. downfield from TMS. Commercial lactates used had specific rotations as follows: S-ethyl lactate: $[\alpha]^{20}$–11.12°; S-methyl lactate: $[\alpha]^{20}$–8.29°; R-methyl lactate $[\alpha]^{23}$+8.350.

EXAMPLE 1

Method A: Formation of Methyl R-2-O—N,N-dimethyl-sulfamyloxypropanoate

R-Methyl lactate (104 g, 1.00 mole) was added dropwise during 30 min. with stirring at –5° to 0° C. to a mixture of sulfuryl chloride (129 mL) and dichloromethane (130 mL) through which was bubbled a slow stream of dry nitrogen. The mixture was allowed to reach 20° C⁻ during 8 hrs. (nitrogen bubbling continued) after which all volatiles were removed in vacuo to constant weight at below 30° C., first at 25 mmHg and then at 0.1 mmHg., to leave the colourless and odorless crude chlorosulfonate (164 g, 81%). A portion was distilled at 0.05 mmHg and showed n.m.r.: 1.71 (d, 3H), 3.83(s, 3H, 5.25 (q, 1H).

Of this, 36.0 g (0.178 m) were dissolved in dry dichloromethane (80 mL). A solution of dimethylamine in tert.butyl methyl ether (2.7 molar, 76 mL, 0.205 mole) was admixed with triethylamine (28.4 mL, 0.205 mole) and 4-dimethylaminopyridine (0.5 g) and was added dropwise with stirring during 1 hr. while keeping the internal temperature below −60° C. Stirring was continued overnight and the temperature allowed to reach 20° C. Water was added to dissolve the suspended solid; the organic layer was separated, dried and the solvents removed. Distillation (bulb-to-bulb) of the residue gave the N,N-dimethylsulfamate, b.p. 80–82° C./0.08 mmHg, yield 24.47 g (65.2%), $\alpha^{21}$+38.6°, suitable for further reaction, n.m.r. 1.56 (3H, d), 2.81 (3H, d), 3.76 (3H, s), and 4.82–4.96 (m, 2H); i.r. 3328, 1760.5, 1357, 1184, 1089, 865. Refractionation gave a material having $[\alpha]^{21}$+33.55°, with little loss. The overall yield from the R-lactate was 50–52%.

EXAMPLE 2

Method B: Formation of S-Ethyl 2-O—N,N-dimethylsulfamylexypropanoate (a) To S-ethyl lactate (43.36 mL, 0.38 mole) and triethylamine (55.75 mL, 0.40 mole) in dry dichloromethane (250 mL), N-methylsulfamyl chloride (see Note) (45.65 g, 0.352 mole) was added with stirring, at a temperature below −40° C., during 30 min. Stirring was continued while the white suspension reached room temperature during a period of 8 hrs. Water and dilute HCl was added with stirring, and the organic layer was separated. Drying and solvent removal, finally at 80° C. at 0.5 mmHg gave the crude N-methylsulfamate derivative (73.28 g, 98% of the theoretical amount) which could not be distilled in vacuo without some decomposition.

(b) This material (57.17 g, ca. 0.271 mole) was dissolved in dry acetone (200 mL), dimethyl sulfate (41 mL, ca. 30% excess) and then dry potassium carbonate (42.78 g, ca. 15% excess) were added, followed by addition of 18-Crown-6 (200 mg, ca. 0.3%/mole), and the whole reaction mixture was stirred. After ca. 0.5 hr. the internal temperature slowly rose from 25° C. to 33° C. and remained at this temperature for 3 hrs. before returning to room temperature. A thick suspension was formed which was stirred at room temperature overnight. The acetone was removed in vacuo, water was added to dissolve inorganic salts, and the product was isolated using CHCl₃. Drying and removal of solvent, followed by fractionation gave the product, b.p. 75–80° C./0.05 mmHg, yield 24.78 g (43.4% overall from ethyl lactate), n.m.r. 1.28(t, 3H), 1.55(d, 3H), 2.85(s, 6H), 4.21(q, 2H) and 4.91(q, 1H) (i.e. no evidence of transesterification); i.r.: 1760.5, 1377, 1185, 948, 794; $[\alpha]^{23}$−27.780.

Note: Both N-methylsulfamyl chloride and the N,N-dimethyl analog mentioned in the next Example were prepared in over 95% yield by the general method given by G. Weiss and G. Schulze, Liebigs Ann. Chem. 1969, 729, 40, by heating under reflux a suspension of the corresponding amine hydrochloride (1 g. mole), sulfuryl chloride (2.1 g. mole) and acetonitrile (200 mL) after adding a catalytic amount (1 mL) of titanium tetrachloride, using a thermostatically controlled water bath and gas trap leading from the condenser, for 1.5 times the period necessary for complete dissolution. In the case of the N-methyl compound this took more than 72 hrs., whereas with the N,N-dimethyl chloride this took less than 8 hrs. (the latter is commercially available). The product was then distilled, after solvent removal, by a bulb-to-bulb method (ice-cooled receiver) at less than 0.5 mmHg (heating bath or oven below 130° C.). The N-methylsulfamyl chloride distilled at 70–75° C./0.1 mmHg and the N,N-dimethylsulfamyl chloride at 40–45° C./0.1 mmHg.

EXAMPLE 3

Method C: Formation of ethyl S-2-O—N,N-dimethylsulfamyloxypropanoate

To a mixture of S-ethyl lactate (63.5 g, 0.54 mole) and N,N-dimethylsulfamyl chloride (77.5 g, 0.54 m) in dry tert-butyl methyl ether (300 mL), was added sodium hydride (see Note) (11.1 g, 0.4625 mole) was added with mechanical stirring under nitrogen during 6 hrs., using a rotating powder dispenser connected to an electric motor (3–5 revs./sec.), keeping the mixture all the time at −10° C. −15° C. (ice/salt). Thereafter the mixture was allowed to reach room temperature (18° C.) very gradually during 10 hrs. Water was added, the organic layer separated and the aqueous layer once extracted with dichloromethane, the organic layers dried and the solvents removed in vacuo. The residue was fractionated at 0.1–0.05 mmHg, collecting at first a forerun distilling up to 50° C. containing recovered ethyl lactate and dimethylsulfamyl chloride in a 3:2 molar ratio (by n.m.r.) and thus containing 0.08 m of the latter. The main fraction distilled at 80–82° C./0.05 mmHg, yield 71.19 g (68.4% on sodium hydride and 70.0% on unrecovered dimethylsulfamyl chloride, $[\alpha]^{12}$: −16.72°—the optical purity (e.e.) as compared with the material obtained by Method B was thus 60.2%.

Note: The sodium hydride must be hydrocarbon-washed free of oil and dried in vacuo. This is best done in a tared stopperable sintered glass funnel which can then be attached to the flask or powder dispenser by balloon or Gooch tubing.

EXAMPLE 4

Ethyl R-2-trifluoromethylsulfonyloxypropanoate

To the sulfamyloxy compound prepared in Example 2 (16.81 g, 74.71 mmol) in dry CCl₄ (40 mL) triflic acid (10.88 g, 72 mmol) was added at 0° C. with vigorous stirring which was continued for 8 hrs. at room temperature. The N,N-dimethylsulfamic acid formed was filtered off and washed with CCl₄, the filtrate was washed with cold 0.5 M NaHCO₃, dried and the solvent removed at room temperature at 23 mm Hg. The residue was fractionated (Teflon column) to give 12.94 g (71.5% yield) of the triflate ester, b.p. 32–34° C./0.07 mmHg, n.m.r. 1.31 (t, 3H), 1.67 (d, 3H), 4.28 (q, 2H); i.r. 1767, 1428, 1217, 1153, 961,. 622; $[\alpha]^{21}$: +43.7°. H. H. Paulsen, P. Himpkamp, and T. Peters; Liebigs Ann. Chem. 1986, 664, for the S-enantiomer prepared using triflic anhydride—pyridine, report b.p. 40.5° C./0.9 mmHg, [α]: −40°; and a commercial source reports [α] −44°±2, for the S enantiomer.

EXAMPLE 5

Ethyl R-2-Fluorosulfonyloxypropanoate

To the sulfamyloxy compound prepared in Example 2 (13.55 g, 60.22 mmol) in dry CCl₄ (35 mL) fluorosulfonic acid (6.1 g, 61 mmol) was added at 0° C., and the whole mixture was stirred vigorously at room temperature for 7 hrs. Very similar results were obtained using trichloroethylene as solvent, instead of $CCl_4$. Working up as in Example 4, and distillation (b.p. 34–36° C./0.1 mmHg) gave the product, yield 9.23 g (82%), n.m.r. 1.31 (t, 3H), 1.56 (d, 3H), 4.25 (t, 2H) and 5.19 (q, 1H), $^{19}F$ n.m.r.: singlet at 98.96 p.p.m.,; i.r. 1760.5, 1447, 1224, 980, 839; $[\alpha]^{16}$: +44.34°, no high resolution [M+] peak.

Inversion Experiments

EXAMPLE 6

Ethyl S-2-acetyloxypropanoate from the R-Triflate

To the above R-triflate (6.73 g, 26.9 mmol) in acetonitrile (15 mL) potassium acetate (3.43 g, 30% excess) was added with stirring. A vigorous exotherm was held in check by water cooling. The whole mixture was stirred at 25–30° for 3 hrs., the solvent removed at 21 mmHg at room temperature, water was added and the product isolated with ether. Fractionation gave the product, b.p. 83–85° C./23 mmHg, yield 3.69 g, $[\alpha]^{22}$–44.78°.

EXAMPLE 7

Ethyl S-2-acetyloxypropanoate from the R-fluorosulfonate

To the above fluorosulfonate (5.04 g, 25.2 mmol) in acetonitrile (13 mL) potassium acetate (3.21 g, 30% excess) was added with water cooling. The reaction was then continued as in Example 6. Fractionation gave the product, b.p. 83–85° C./23 mmHg, yield 3.15 g, $[\alpha]^{21}$: –45.7°.

Conclusion from Inversion Experiments

Authentic ethyl S-2-acetyloxypropanoate was prepared from S-ethyl lactate by the customary method (1.5 equiv. acetic anhydride, 3 equivs. of pyridine, 90–100°/30 min., usual working up). After distillation the product had $[\alpha]^{21}$– 50.61°. It follows that proceeding via sulfamate ester as prepared by the two-step Method B, overall e.e. was 88.5% when going via the triflate and 90.3% when going via the fluorosulfonate; in both cases three steps, two of them inversions.

EXAMPLE 8

Methyl S—O—N,N-dimethylsulfamyloxypropanoate

This compound was prepared from S-methyl lactate via the two-step Method B as described above for the ethyl ester, using the same molar proportions of reagents. The intermediate N-monomethylsulfamate could be distilled at 128–130° C./0.5 mmHg, n.m.r. 1.56 (3H, d), 2.81 (3H, d), 3.76 (3H, s) and 4.82–4.96 (m, 2H), i.r. 3328, 1760.5, 1357, 1184, 1089, 865; $[\alpha]^{21}$: –56.46°. The dimethylsulfamate showed $[\alpha]^{21}$–33.50°.

EXAMPLE 9

Methyl R-2-fluorosulfonyloxypropanoate

This compound was prepared from the foregoing dimethylsulfamate by reaction with fluorosulfonic acid in $CCl_4$ exactly as described for the S-ethyl dimethylsulfamate in Example 5. The product had b.p. 35–36° C./0.08 mmHg; n.m.r. 1.70 (d, 3H), 3.83 (s, 3H), 5.22 (q, 1H), $^{19}F$ n.m.r.: singlet at 57.19 p.p.m.; i.r. 1773, 1447, 1236, 986; it also showed a very small M.S. peak (M+): 186.0043 (calc. for $C_4H_7FO_5S$: 186.0048) and had $[\alpha]^{18}$+41.23°.

EXAMPLE 10

Methyl S-fluorosulfonyoxypropanoate

This compound was prepared from the product of Example 1 exactly as described in Example 9 for its R-enantiomer; it showed $[\alpha]^{21}$–44.35°.

EXAMPLE 11

Methyl R-2-(4-chloro-2-methylphenoxy)propanoate, "Mecoprop Methyl" and "Mecoprop" (R-2-(4-Chloro-2-methylphenoxy-propanoic acid)

(a) 4-Chloro-2-methylphenol (8.56 g, 60 mmol) was dissolved in 3.167M aqueous KOH (18.95 mL, theoretical amount) and the solution evaporated at 80° C./25 mmHg to a viscous syrup. To this was added diethylene glycol dimethyl ether (12 mL) and the solution again evaporated at ca. 95° C./25 mmHg to a volume of ca. 11 mL. The remaining syrup was diluted with acetonitrile (5 mL), and the solution added at –20° C. with stirring to a solution of the S-fluorosulfonate prepared in Example 10 (9.3 g, 50 mmol) in acetonitrile (15 mL). After continuing to stir at room temperature overnight the solvent was removed at 25 mmHg at room temperature, water was added and the product isolated with dichloromethane. Fractionation gave 9.22 g (80.6%) of product, b.p. 77–79° C./0.02 mmHg, n.m.r. 1.60 (d, 3H), 2.23 (s, 3H), 3.72 (s, 3H), 4.68 (q, 1H), 6.56 (d, 1H) and 7.02–7.28 (m, 2H); i.r. 1761, 1496, 1250, 1149, 815; $[\alpha]^{18}$+26.88°.

(b) The above ester (2.33 g) in dioxan (25 mL), water (10 mL) and conc. HCl (1.5 mL) was heated under reflux for 24 hr., after which the solution was evaporated at 80–90° C./25 mm. The residue, in ether was separated into acidic ($NaHCO_3$) (1.93 g) and neutral (0.17 g) portions. The former was recrystallised twice from hexane to give the acid (1.76 g), m.p. 92.5–93° C., $[\alpha]^{21}$ (acetone, c 1) +26.29°. M. Matell, Arkiv Kemi 1952, 4, 325 reports m.p. 95–96° and $[\alpha]^{19}$+29.3° (acetone) for the R-acid obtained by resolution. The overall e.e. is thus 90%.

EXAMPLE 12

"Butyl Mecoprop"

(a) R-n-Butyl lactate

A mixture of R-methyl lactate (52 g), n-butanol (65 mL, 1.4 equiv.), methylcyclohexane (150 mL) and Amberlyst 15 (5 g) was fractionated through a Widmer column for 10 hrs. to distil off first the methanol/methylcyclohexane azeotrope and then the n-butanol/methylcyclohexane azeotrope (finally to 93°). The mixture was filtered through a short Florisil column and the product, after evaporating remaining solvents, was fractionated, b.p. 86–90° C./22 mmHg, yield 56.8 g (81.5%), $[\alpha]^{18}$: +13.4°. A commercial source for the S-enantiomer gives $[\alpha]^{20}$: –12°.

(b) R-n-Butyl 2-O—N,N-dimethylsulfamyloxy- propanoate

The above was treated with sulfuryl chloride and dichloromethane exactly (same molar quantities) as described for the methyl ester in Example 1, and the crude vacuum-dried product in dichloromethane treated at below –60° C. with 1.2 equivalent each of dimethylamine and of triethylamine in toluene (4.1M in dimethylamine). Fractionation (105–110° C./0.1 mmHg) gave the dimethylsulfamate in 56.75% overall yield, n.m.r. 0.90 (t, 3H), 1.30–1.70 (m, 7H), 2.87 (s, 6H), 4.15 (t, 2H), 4.93 (q, 1H); i.r. 1761, 1372, 1183, 950, 573; $[\alpha]^{20}$+28.22°.

(c) S-n-Butyl 2-fluorosulfonyloxypropanoate

The aforegoing dimethylsulfamate was treated with fluorosulfonic acid in $CCl_4$ exactly as in previous Examples, except that the reaction appeared to be more sluggish. Very similar results were obtained using trichloroethylene as solvent. After stirring for 10 hrs. at 21° C., filtration and the usual working-up the fluorosulfonate was obtained in 77.5% yield, b.p. 48–50° C./0.1 mmHg, n.m.r. 0.91 (t, 3H), 1.36 (m, 2H), 1-60-1.67 (m, 4H), 1.685 (d, 3H), 4.21 (t, 2H), 5.20 (q, 1H), $^{19}F$ n.m.r.: singlet at 0.00 p.p.m.; i.r. 1767.5, 1450, 975.7, 580; $[\alpha]^{20}$: –38.98°.

(d) R-n-Butyl 2-(4-chloro-2-methylphenoxy)propanoate

A solution of potassium 4-chloro-2-methylphenoxide, from 5.92 g of the phenol, was prepared as described in Example 11, but this time in dimethylformamide instead of diglyme. The solution, diluted with acetonitrile was added below –20° C. with stirring to 7.98 g of the aforementioned fluorosulfonate in ca. 10 mL acetonitrile. The usual working-up and distillation (100–105° C./0.05 mmHg) gave 8.02 g (71.4%) of the product, n.m.r. 0.87 (t, 3H), 1.10–1.49 (m, 4H), 1.58 (d, 3H), 2.22 (s, 3H), 4.12 (t, 2H), 4.80 (q, 1), 6.60 (q, 1H), 7.05 (m, 2H); i.r. 1761, 1495, 1189, 813, 664; $[\alpha]^{20}$+14.57°.

EXAMPLE 13

R-Dimethyl 2-fluorosulfonyluxybutane-1,4-dioate

S-2-Hydroxybutane-1,4-dioic acid (S-malic acid) was converted into its dimethyl ester using the method of R. O. Clinton and S. C. Laskovsky (J. Amer. Chem. Soc. 1948, 70, 3135). Even with this mild method the formation of the elimination product, dimethyl fumarate could not be avoided; the elimination product was separated from the diester by refluxing the latter at 0.1 mmHg under a cold finger condenser, thus subliming out the highly crystalline byproduct, followed by distilling off the desired product.

The diester (38.94 g, 0.24 mole) was mixed with dichloromethane (240 mL) and triethylamine (34.5 mL, 0.26 mole) was added. The solution was cooled to below –40° C. and with stirring methylsulfamyl chloride (33.8 g, 0.26 mole) was added with stirring at that temperature. Thereafter, the solution was stirred overnight reaching room temperature, water was added, the organic layer washed with dilute $NaHCO_3$, dried and the solvent removed in vacuo, leaving the crude N-methylsulfamate ester (53 g, 87.5%) which crystallised. This product (52.8 g) was suspended in diethyl ether (120 mL) and iodomethane (38 mL). Freshly prepared and vacuum-dried silver oxide (58 g, 0.25 mole) was added with stirring and cooling, keeping the internal temperature at 25–30° C. At first, a pasty lower layer resulted, followed by a suspension of brown solid. The suspension was heated under reflux for 1 hr., filtered, the filtrate concentrated and redissolved in $CCl_4$, whereupon more dimethyl fumarate separated. The filtrate was concentrated in vacuo and the residue kept in a Kugelrohr tube (oven temp. 80–90° C.) at 0.1 mmHg for 2 hrs. to sublime off more elimination product, leaving 24.7 g of the crude N,N-dimethylsulfamate ester which partly decomposed on attempted distillation, but was estimated by high vacuum distillation of a small sample to contain 14.6 g of usable material.

The N,N-dimethylsulfamate ester was dissolved in $CCl_4$ (40 mL), the solution cooled to 0° C. and fluorosulfonic acid (5.7 g) was added with stirring. The whole mixture was stirred at room temperature for 2 days, the $CCl_4$ solution decanted from the gum and washed with ice-cold dilute $NaHCO_3$. Concentration in vacuo and distillation of the residue gave 3.2 g of the R-fluorosulfonyloxy diester, b.p. 70–85° C./0.1 mmHg, $[\alpha]^{20}$+28.94°, n.m.r. 3.04 (d, 2H), 3.74(s ,3H) 3.85 (s, 3H), 5.51 (t, 1H) $^{19}F$ n.m.r.: 7.66 (s) p.p.m.; i.r. 1749, 1446, 1038, 972, 841. Reaction of this with an excess of O-benzylhydroxylamine exactly as described by R. W. Feenstra and his co-workers (Tetrahedron Lett. 1987, 28, 1215) for the corresponding S-triflate gave S-dimethyl 2-benzyloxyaminobutane-1,4-dioate which could not be distilled, but which after chromatography and drying at 40–50° C./0.1 mmHg showed n.m.r. 2.56–2.66 (octet, 2H), 3.66 (s, 3H), 3.77 (s, 3H), 4.00 (m, 1H), 4.67 (s, 2H) 6.18 (m, 1H), 7.30 (s, 5H) in—excellent agreement with the data reported for the Renantiomer (R. W. Feenstra and co-workers, Tetrahedron Lett. 1987, 28, 1215).

EXAMPLE 14

R-Ethyl 2-fluorosulfonyloxy-4-phenylbutanoate (S)-2-Hydroxy-4-phenylbutanoic acid (F. Nerdel and H. Rachel, Chem. Ber. 1956, 89, 671) was esterified in the usual manner using ethanol and a small amount of sulfuric acid as described for the (R)-enantiomer (M. R. Attwood, C. H. Hassall, A. Krohn, G. Lawton, R. Radshaw, J. C. S. Perkin 1, 1986, 1011) with passage of the returned ethanol over a bed of molecular sieves. The resulting ethyl ester had b.p. 95–97° C./0.03 mmHg and showed $[\alpha]^{25}$+8.75° (e.e. 88%). To this (9.86 g, 47.4 mmol) and methylsulfamyl chloride (5.0 mL, 60 mmol) in dichloromethane (25 mL) was added with stirring at –40° to –45° C. triethylamine (6.23 mL, 1.3 equiv.) in dichloromethane (25 mL) during 0.5 hr. The mixture was allowed to reach room temperature overnight, water (4 mL) was added with stirring to destroy excess methylsulfamyl chloride, the organic layer was washed with dilute HCl and water, dried and the solvent removed finally in vacuo to leave crude product (17.3 g). The TLC of this (1:5 ethylacetate-cyclohexane, $SiO_2$ plates) showed absence of starting ester, one main spot and also some much less polar by product, all u.v.—light-visible). The latter could be removed almost completely by shaking with boiling hexane (30 mL), cooling and decanting the hexane layer; this was repeated twice, leaving after drying in high vacuum crude (S)-Ethyl2-methylsulfamyloxy-4-phenylbutanoate (12.07 g., 40 mmol) i.r.: 3300, 1748, 1180 cm$^{-1}$. To this, in acetone (25 mL), dry potassium carbonate (7.19 g, 1.3 equiv.) dimethyl sulfate (6.1 mL, 1.6 equiv.) and tetraethylammonium bromide (0.16 g) were added at 25° C. and the whole stirred for 15 hr. monitoring progress of the reaction by TLC. At the beginning there was a slight (4° C.) rise in temperature which then subsided. Excess of dimethyl sulfate was then destroyed by adding triethylamine (4 mL) with cooling below 20° C. The acetone was removed in vacuo, and the product isolated with diethyl ether (2 extractions). The dried extracts were passed through a short column (10 g) of Florisil, and the solvent removed, finally in a high vacuum, to leave crude (S)-Ethyl 2-N,N-dimethylsulfamyloxy-4-phenylbutanoate (9.47 g, 30.06 mmol) which was practically pure by TLC (slightly less polar than the starting material). Material from another run which could be distilled in small amount (some decomposition) at ca. 155–160° C./0.03 mmHg, showed n.m.r. 7.18–7.3(5H, m, arom), 4.22(1H, m), 2.90(6H, s, N-Me), 2.7–2.8(4H, m). 2.2(2H, m) and 1.25 (3H, t, Me) p.p.m.; i.r.: 1761, 1376, 1174 and 752 cm$^{-1}$.

This product was dissolved in dry 1,2,-dichloroethane (32 mL), the solution cooled to below +10° C., and fluorosulfonic acid (3.15 g, 1.05 equiv.) was added with stirring. The dark mixture was left at room temperature for 48 hr. during which crystals appeared. The reaction was followed by TLC which showed gradual disappearance of starting material; the product showed as negative (white) spot which became apparent only after 6–12 hrs. in an iodine chamber.

After adding another 0.43 g. of fluorosulfonic acid the starting material was completely consumed after another 10 hr. The liquid was decanted from the crystalline dimethylsulfamic acid and the latter washed with small amount of dichloromethane. The combined liquid was washed twice with ice-cold 0.5 N sodium bicarbonate solution and then with water, dried and passed through Florisil (5 g), eluting with more $CH_2Cl_2$. After solvent removal in vacuo the product was carefully fractionated using a jacketed flask (H. J. E. Loewenthal, "Guide for the Perplexed Organic Experimentalist", Wiley, 2nd Edition, 1990, p. 196) having a Teflon column to give (R)-Ethyl2-fluorosulfonyloxy-4-phenylbutanoate, yield 3.83 g, b.p., 105–110° C./0.03 mmHg, $[\alpha]^{20}$+10.6 ($CH_2Cl_2$), n.m.r.: 7.17–7.32 (5H, m, arom.), 5.09 (1H, t), 4.24 to 4.28 (2H, m), 2.30–2.61 (4H, m), 1.30 (3H, t, Me), 19F n.m.r. : –0.001(s) p.p.m., i.r.: 1767, 1447, 1229 and 980 $cm^{-1}$.

EXAMPLE 15

S,S-N-(1-ethoxycarbonyl-3-phenylpropyl)alanine

The above (R)-fluorosulfonate (3.83 g) was added in dry acetonitrile (10 mL) with stirring at –10° C. to L-alanine benzylester (2.51 g) and triethylamine (1.62 g) in dry acetonitrile (8 mL). The stirred solution was allowed to reach room temperature during 2 hr. and then kept at 40° C. for 0.5 hr. The solvent was removed in vacuo, water was added and the product twice extracted with diethyl ether. Drying and removal of solvent in vacuo left a residue which was dissolved in ethanol (20 mL). Palladium on charcoal (10%, 0.4 g) was added, and the whole shaken in hydrogen at ca. 35 p.s.i. The required amount of gas was absorbed in 12 min. After filtration from catalyst and removal of tetrahydrofuran—ethyl acetate, to give the product (desproline enalapril), 1.8 g, m.p. 146.5–147° C., $[\alpha]^{25}$+30° (MeOH). C. R. Urbach and R. Henning (Tetrahedron Lett., 1984, 25, 1143) report: m.p. 148–150° C., [α]+28.20 (MeOH); practically the same data was obtained by J. S. Kaltenbronner, D. M. John, U. Kroll (Org. Prep. Proc. Intern. 1983, 15, 35).

What is claimed is:

1. A method of substituting a hydroxy group attached to a chiral carbon atom bearing an electron withdrawing group in a hydroxy compound with a leaving group selected from fluorosulfonate and perfluoroalkylsulfonates, where the substitution occurs with inversion of configuration and substantial retention of the chirality, which comprises the steps of:

(a) converting said hydroxyl group to an O—N,N-dialkylsulfamate ester thereof, and (b) reacting said O—N,N-dialkylsulfamate ester, optionally in a suitable inert solvent, with 1±0.2 equivalent of either perfluoroalkylsulfonic acid or fluorosulfonic acid.

2. The method according to claim 1 wherein said perfluoroalkylsulfonic acid is trifluoromethylsulfonic acid.

3. The method according to claim 1 or 2 wherein said hydroxy group is in the α-position to a carboxylic ester group.

4. The method according to claim 1 wherein the hydroxy compound is an ester of lactic acid or a diester of malic acid.

5. The method according to claim 1 wherein the dialkylsulfamate ester in step (a) is prepared by reacting the starting hydroxy compound with a corresponding dialkylsulfamic acid or a reactive derivative thereof.

6. The method according to claim 5 wherein the dialkylsulfamate ester in step (a) is prepared by adding a strong base to a mixture of said hydroxy compound and a reactive derivative of a dialkylsulfamic acid in an inert solvent.

7. The method according to claim 6 wherein the reactive derivative of the dialkylsulfamic acid is a dialkylsulfamyl halide and the reaction is carried out under phase transfer conditions.

8. The method according to claim 6 wherein the strong base is an alkali metal hydride.

9. The method according to claim 6 wherein the strong base is a hindered Grignard reagent.

10. The method according to claim 6 wherein the strong base is an amide or a substituted amide of an alkali metal or alkaline earth metal.

11. The method according to claim 6 wherein the strong base is an alkoxide, an alkoxide complex, or an amide-alkoxide complex of an alkali metal or alkaline earth metal.

12. The method according to claim 1, wherein the dialkylsulfamate ester in step (a) is prepared by reacting the starting hydroxy compound with an N-alkylsulfamyl chloride in the presence of a base to give the corresponding N-monoalkylsulfamate, which is then alkylated by an alkylating agent in a suitable solvent, in the presence of a base and a phase transfer catalyst.

13. The method according to claim 1 wherein the dialkylsulfamate ester in step (a) is prepared by reacting the starting hydroxy compound with sulfuryl chloride to give the corresponding chlorosulfonate, and then adding a dialkylamine or a mixture of a dialkylamine and a tertiary amine, at a temperature of about –40° C. or below.

14. The method according to claim 1, wherein the reaction in step (b) is carried out without a solvent, at a temperature between –50° and +30° C.

15. The method according to claim 1, wherein the reaction in step (b) is carried out in an inert solvent, at a temperature between –50° and +30° C.

16. The method according to claim 15, wherein the reaction in step (b) is carried out in a chlorinated hydrocarbon solvent.

17. The method according to claim 16 wherein the chlorinated hydrocarbon is carbon tetrachloride.

18. The method according to claim 1, wherein said O—N,N-dialkylsulfamate ester obtained in step (a) is reacted in step (b) with trifluoromethylsulfonic acid or with fluorosulfonic acid in a chlorinated hydrocarbon solvent, with vigorous stirring or agitation, whereby a suspension of crystalline dialkylsulfamic acid in the solution of the product is obtained, said crystalline byproduct is separated by filtration and the triflate or fluorosulfonate product is isolated by distillation.

19. The method according to claim 18, wherein said chlorinated hydrocarbon solvent is carbon tetrachloride and said dialkylsulfamate ester is a O—N,N-dimethylsulfamate ester.

20. The method according to claim 1 wherein the electron withdrawing group is selected from the group consisting of carboxylic ester, carbonyl and cyano.

21. R-Ethyl 2-fluorosulfonyloxypropanoate.

22. R-Methyl 2-fluorosulfonyloxypropanoate.

23. S-Methyl 2-fluorosulfonyloxypropanoate.

24. R-n-Butyl 2-fluorosulfonyloxypropanoate.

25. R-Dimethyl 2-fluorosulfonyloxybutan-1,4-dioate.

\* \* \* \* \*